(12) United States Patent
Okuno et al.

(10) Patent No.: US 10,433,800 B2
(45) Date of Patent: Oct. 8, 2019

(54) RADIOGRAPHIC APPARATUS

(71) Applicant: SHIMADZU CORPORATION, Nakagyo-Ku, Kyoto-Shi, Kyoto (JP)

(72) Inventors: Tomoharu Okuno, Kyoto (JP); Hideki Fujii, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 273 days.

(21) Appl. No.: 15/541,899

(22) PCT Filed: Jan. 9, 2015

(86) PCT No.: PCT/JP2015/050548
§ 371 (c)(1),
(2) Date: Jul. 6, 2017

(87) PCT Pub. No.: WO2016/111015
PCT Pub. Date: Jul. 14, 2016

(65) Prior Publication Data
US 2018/0000436 A1  Jan. 4, 2018

(51) Int. Cl.
*A61B 6/00* (2006.01)
*A61B 6/02* (2006.01)

(52) U.S. Cl.
CPC ............ *A61B 6/4452* (2013.01); *A61B 6/025* (2013.01); *A61B 6/027* (2013.01); *A61B 6/4021* (2013.01);
(Continued)

(58) Field of Classification Search
CPC ....... A61B 6/4452; A61B 6/025; A61B 6/027; A61B 6/4021; A61B 6/4464; A61B 6/467; A61B 6/54; A61B 6/4233
See application file for complete search history.

(56) References Cited

U.S. PATENT DOCUMENTS

| 2012/0002790 A1* | 1/2012 | Tanaka | A61B 6/025 378/198 |
| 2015/0250441 A1* | 9/2015 | Okuno | A61B 6/06 378/62 |
| 2018/0014808 A1* | 1/2018 | Masuda | A61B 6/035 |

FOREIGN PATENT DOCUMENTS

| JP | 6-269437 | 9/1994 |
| JP | 2002-263093 | 9/2002 |

(Continued)

OTHER PUBLICATIONS

PCT/JP2015/050548, ISR and Written Opinion, dated Mar. 31, 2015, 7 pages—Japanese; 2 pages—English.

*Primary Examiner* — Christine S. Kim
(74) *Attorney, Agent, or Firm* — Andrew F. Young, Esq.; Lackenbach Siegel, LLP

(57) ABSTRACT

A radiography apparatus is provided in which delays in imaging do not occur due to the influence of preliminary preparation of a radiation detector. The FPD 4 receives a signal from an X-ray tube control unit 6 and then completes preliminary preparation for the detection of radiation during accelerated movement of an X-ray tube 3 or the FPD 4. That is, the accelerated movement of the X-ray tube 3 or the FPD 4 and the preliminary preparation for the detection of radiation are carried out simultaneously. This enables imaging to be started immediately after the start of constant speed movement of the X-ray tube 3 or the FPD 4 without having to wait for constant speed movement thereof to start preliminary preparation of the FPD 4 as in conventional apparatuses. As a result, delays in imaging do not affect the radiation image.

5 Claims, 11 Drawing Sheets

(52) U.S. Cl.
CPC ............ *A61B 6/4464* (2013.01); *A61B 6/467* (2013.01); *A61B 6/54* (2013.01); *A61B 6/4233* (2013.01)

(56) References Cited

FOREIGN PATENT DOCUMENTS

| | | |
|---|---|---|
| JP | 2005-3735 | 1/2005 |
| JP | 2011-4857 | 1/2011 |
| JP | 2012-100738 | 5/2012 |
| JP | 2012-135525 | 7/2012 |

* cited by examiner

US 10,433,800 B2

RADIOGRAPHIC APPARATUS

CROSS REFERENCE TO RELATED APPLICATIONS

This application relates to and claims priority Ser. No.: PCT/JP2015/050548 filed Jan. 9, 2015, the entire contents of which are incorporated herein by reference.

FIGURE SELECTED FOR PUBLICATION

FIG. 5

BACKGROUND OF THE INVENTION

Field of the Invention

The present invention relates to a radiography apparatus that performs an imaging of a subject using a radiation and particularly relates to the radiography apparatus that performs imaging while shifting (shifting) the imaging system.

Description of the Related Art

A medical facility equips a radiography apparatus to obtain an image of a subject using radiation. Referring to FIG. 7, a conventional radiography apparatus comprises a pedestal supporting a table 52 on which the subject is loaded, a radiation source 53, and a radiation detector 54 installed inside the table, which detects the radiation, which (e.g., Patent Document 1, Patent Document 2).

The inventor sets forth briefly an operation of the above apparatus. Referring to FIG. 8, when an operator directs the apparatus to perform the radiation imaging, the signal including the directive of the operator is sent to a control device for the radiation source 53 (the radiation source control element 56) (refer to (1) in FIG. 8). When the condition of the radiation source 53 is in the normal state in which the radiation source 53 is available to perform irradiation of radiation, the radiation source control element 56 sends the signal indicating such state, in which the radiation irradiation is ready for irradiation, to the radiation detector 54 (refer to (2) in FIG. 8). The radiation detector 54 initiates a pre-preparation to detect the radiation when receives the signal from the radiation source control element 56. When the pre-preparation is completed, the radiation detector 54 sends the signal indicating such state to the radiation source control element 56 (refer to (3) in FIG. 8). The radiation source control element 56 starts to irradiate radiation following the signal receiving (refer to (4) in FIG. 8). Accordingly, the conventional apparatus performs to irradiate radiation once it is confirmed, by exchanging the signal between the radiation source control element 56 and the radiation detector 54 prior to imaging, that the radiation source 53 and the radiation detector 54 are correctly operable each other.

RELATED PRIOR ART DOCUMENTS

Patent Document

Patent Document 1: JP Patent Published 2002-263093 A
Patent Document 2: JP Patent Published 2012-100738 A

ASPECTS AND SUMMARY OF THE INVENTION

Objects to be Solved

However, there are following problems remain in the conventional apparatus.

Specifically, such conventional apparatus has not been fully considered in regard to an operable imaging while shifting the imaging system. Here, the imaging system means the radiation source 53 and the radiation detector 54. Specifically, aspects in which the imaging system is being shifted includes an aspect in which only the radiation source 53 shifts, an aspect in which only radiation detector 54 shifts and an aspect which both radiation source 53 and the radiation detector 54 shift.

In the operational explanation relative to the above apparatus, the imaging system is stilled to perform imaging, but the radiation imaging must be taken continuously while the imaging system is shifting, depending on an imaging application such as a tomographic imaging. According to such imaging system, once the stilled imaging system is accelerated and when the imaging system is in the constant speed, the imaging is performed. Otherwise, no clear tomographic image can be taken.

According to the conventional apparatus, the continuous imaging of the radiation images starts at the time of beginning of shifting of the imaging system at the constant speed when the radiation images are continuously taken. Relative to the tomographic imaging, images of the subject must be taken from a variety of directions. The longer the time pasts after while the imaging system has shifted at the constant speed when the continuous imaging starts, the broader the shifting range of the imaging system is, so that the imaging direction can be limited. To prevent such incident, the first imaging of the radiation images is performed coincidentally at the time when the imaging system starts the constant-speed-shifting. Then the following continuous radiation imaging is performed every time when the constant time passes from the starting point when the first radiograph is taken.

The inventor sets forth the way how the first radiograph is taken in such continuous imaging operation. Referring to FIG. 9, when an operator directs the apparatus to perform the tomographic imaging, the signal indicating the directive of the operator is sent to a shifting control element 58 of the imaging system and the shifting control element 58 starts shifting the imaging system (refer to (1) in FIG. 9).

On the other hand, the signal indicating the directive of the operator is also sent to a control device (radiation source control element 56) of the radiation source 53 (refer to (2) in FIG. 9). Even when the condition of the radiation source 53 is in the normal state ready to irradiate radiation, the radiation source control element 56 does not determine that the radiation is available. The reason is that the imaging cannot be performed w some case because the imaging system is under acceleration. Following receiving the signal indicating the directive of the operator, the radiation source control element 56 waits until receives the signal, indicating that the shifting of the imaging system is at the constant speed, from the shifting control element 58 of the imaging system. The radiation source control element 56 sends the signal indicating the incident to the radiation detector 54 (refer to (4) in FIG. 9) when the radiation source control element 56 receives the signal from the shifting control element 58 (refer to (3) in FIG. 9), The radiation detector 54 initiates a pre-preparation to detect the radiation when receives the signal from the radiation source control element 56. When the pre-preparation is completed, the radiation detector 54 sends the signal indicating such state to the radiation source control element 56 (refer to (5) in FIG. 9). The radiation source control element 56 starts to irradiate radiation following the signal receiving (refer to (6) in FIG. 9). The radiation detector 54 needs just 100 msec to complete the pre-preparation.

The time needed for the pre-preparation of the radiation detector 54 can be, however, an issue when the continuous imaging of the radiographs is performed while shifting the imaging system. FIG. 10 is a timing chart illustrating operations of (4), (5), (6) indicated in FIG. 9. Referring to FIG. 10, the imaging of the radiograph does not start until the imaging systems 3, 4 are at the constant speed and then the pre-preparation of the FPD 4 is further completed.

The tomographic image can be achieved by reconstructing the radiographs that are continuously taken. At this time, the event in which the respective radiographs are taken from a specific imaging direction is subject to the reconstruction processing. FIG. 11A is illustrating the timing of the ideal radiography. It is ideal that an imaging of the first imaging starts at the time when the imaging system starts constant-speed-shifting.

Relative to such condition, the pre-preparation of the radiation detector 54 is, however, out of consideration. Specifically, referring to 11B, the imaging of the first radiograph delays for just 100 msec. The imaging system shifts within 100 msec, so that the imaging direction of the first radiograph shifts from the predicted direction. The subsequent imaging of the radiograph shifts by 100 msec, so that imaging of a series of images cannot be accomplished by positioning the imaging system at the ideal location. Consequently, the imaging direction relative to the series of radiographs shifts from the predicted direction. Such shift of the imaging direction results in providing the unfocused tomographic image.

To solve the above problems, one purpose of the present invention is to provide a radiography apparatus operative without a delayed imaging due to an impact of the pre-preparation of a radiation detector.

Means for Solving the Problem

The present invention comprises the following structures to solve the above problem.

Specifically, a radiography apparatus of the present invention comprises
a radiation source that irradiates a radiation; a detection means that detects the radiation transmitted through the subject; an input means that allows an operator to input a directive to start imaging; a shifting means that transfers first the suspended radiation source or the suspended detection means in an acceleration-shifting and followed by changing into the constant-speed-shifting when the directive of imaging start is input to the input means; and a radiation source control means that outputs a signal, indicating that the radiation source is ready to irradiate the radiation, to the detection means when the input means receives the directive to start imaging; wherein the detection means is in the detectable state promptly following the radiation source or the detection means is in the constant-speed-shifting by initiating the pre-preparation while the radiation source or the detection means is under the acceleration-shifting.

Action and Effect

According to the present invention, the radiography apparatus not subject to a delayed imaging due to the effect of the pre-preparation of the detection means can be provided. According to the present invention, the detection means starts the pre-preparation for the radiation detection while the radiation source or the detection means is acceleration-shifting following receiving the signal from the radiation control means. Specifically, according to the present invention, an acceleration-shifting of the radiation source or the detection means and the pre-preparation for the radiation detection are implemented simultaneously. Therefore, differently from the conventional device, the imaging is ready right after start of the constant-speed-shifting without initiating the pre-preparation of the detection means after the radiation source or the detection means shifts at the constant speed. Consequently, no effect due to the delayed imaging appears in the radiograph.

Further, according to the above radiography apparatus, it is further preferable that the detection means sends back the signal, indicating that the radiation detection is available, to the radiation source control means.

Action and Effect

The above structure illustrates further specifically the detection means of the present invention. The radiation source control means enables to irradiate a radiation after send-back of the signal if the detection means executes the send-back operation, so that no irradiation of the radiation takes place erroneously before start of the constant-speed-shifting.

Further, according to the above image processing device, it is further preferable that the detection means comprises a memory means that stores a waiting time between the time when the signal is received from the radiation source control means and the time when the radiation source or the detection means transfers to the constant-speed-shifting and the pre-preparation time for the pre-preparation of the detection means to detect the radiation, in which the detection means implements the pre-preparation of the detection means at the time after passed the time obtained by subtracting the pre-preparation time from the shifting waiting time from when receiving signal from the radiation source control means and then the send-back operation is executed when the pre-preparation is completed.

Action and Effect

The above structure illustrates further specifically the detection means of the present invention. When the detection means completes the pre-preparation and executes the send-back operation at the time when the shifting waiting time passes from the time when receiving the signal from the radiation source control means, an occurrence of an unnecessary radiation detection period is prevented and a necessary radiation detection time can be ensured.

In addition, relative to the above radiography apparatus, it is preferable that a while in which the shifting means is shifting the radiation source or the detection means in the acceleration-shifting is longer than a while which the detection means needs for the pre-preparation for detection of the radiation Action and Effect The above structure illustrates further specifically the aspects of the present invention. When the while in which the shifting means is shifting the radiation source or the detection means in the acceleration-shifting is longer than the while which the detection means needs for the pre-preparation, the detection means can complete absolutely the pre-preparation while the detection means is waiting the completion of the acceleration-shifting.

Further, according to the above radiation imaging apparatus, it is further preferable that the radiographic device comprises an image generation means that generates the radiograph based on an output from the detection means, and a tomographic image generation means that generates the tomographic image by superimposing the series of radiographs to each other, which are continuously imaged while the radiation source and the detection means are shifting in the opposite direction to each other.

Action and Effect

The structure of the present invention can be applied to a known tomosynthesis apparatus.

Effect of the Invention

According to the present invention, the radiography apparatus not subject to a delayed imaging due to the effect of the pre-preparation of the detection means can be provided. According to the present invention, the detection means completes the pre-preparation for the radiation detection while the radiation source or the detection means are acceleration-shifting following receiving the signal from the radiation control means. Specifically, according to the present invention, acceleration-shifting of the radiation source or the detection means and the pre-preparation for the radiation detection are implemented simultaneously and are completed at the same time. Therefore, differently from the conventional device, the imaging is ready right after start of the constant-speed-shifting without initiating the pre-preparation of the detection means after the radiation source or the detection means constant-speed-shifts. Consequently, no effect due to the delayed imaging appears in the radiograph.

The above and other aspects, features and advantages of the present invention will become apparent from the following description read in conjunction with the accompanying drawings, in which like reference numerals designate the same elements.

DETAILED DESCRIPTION OF THE PREFERRED EMBODIMENTS

Various operations may be described as multiple discrete operations in turn, in a manner that may be helpful in understanding embodiments of the present invention; however, the order of description should not be construed to imply that these operations are order dependent.

Hereafter, the inventor illustrates the best mode of Embodiment of the present invention referring to FIGs. Further, an X-ray corresponds to the radiation of the present invention. FPD stands for Flat Panel Detector. An X-ray imaging apparatus according to the present invention is an apparatus capable of imaging a tomographic image based on the same discipline for a digital tomosynthesis apparatus.

Embodiment 1

<Entire System of the X-Ray Imaging Apparatus>

Figure 1:
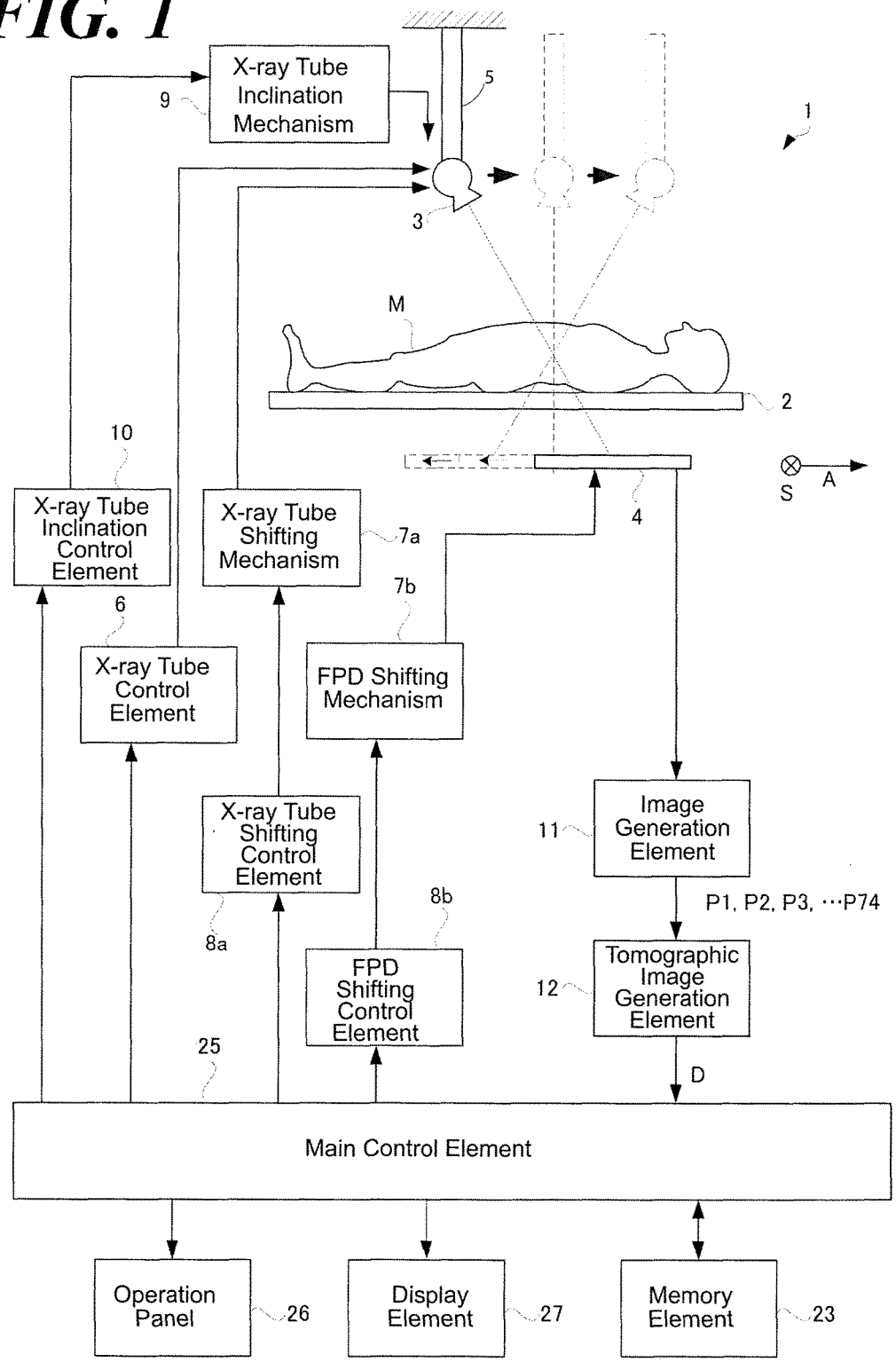
FIG. 1 is a functional block diagram illustrating the entire structure of an X ray imaging apparatus according to the Embodiment 1.

Referring to FIG. 1, an X-ray radiography apparatus according to the Embodiment 1 comprises; a table 2, on which a subject M in the decubitus position is laid, an X-ray tube 3 to irradiate an X-ray, which is mounted above the table 2 (one side); and a FPD 4 to detect the X-ray transmitted through the subject M and to output a detection signal, which is mounted under the table 2. The FPD 4 has a rectangular shape with 4 sides along with either the axis direction A of the body or the side direction S of the body of the subject M. One of the FPDs 4 is used for imaging and when the imaging is carried out in the decubitus position, such detector is in place in the opposite side of the table 2 against the subject M. The detection surface of the FPD 4 to detect the X-ray is facing to the X-ray tube 3 and the subject M. In addition, the X-ray tube 3 irradiates the X-ray quadrangular pyramid beam toward the FPD 4. Accordingly, the FPD 4 receives the X-rays on, the whole detection surface. Such FPD 4 according to the present invention plays functionally an important role. The inventor sets forth the detail thereof later. The X-ray tube 3 corresponds to the radiation source of the present invention and the FPD 4 corresponds to the detection means of the present invention to detect the X-ray transmitting the subject M.

The FPD is a direct conversion type X-ray detector. Specifically, the FPD 4 comprises a conversion layer, e.g., CdTe (formed from cadmium and tellurium), that converts an X-ray to an electron and a pair of holes (a pair of charge carriers). Charge carriers generated in the conversion layer are trapped by each detection element and cumulated. When the signal to output the charge carriers to the detection element is sent, the detection element outputs the cumulated charge carriers therein as signals.

The post 5 is extending from the ceiling of the examination room toward the floor surface and supporting the X-ray tube 3. The X-ray imaging apparatus having such post 5 is called a radiation source hanging type. The X-ray tube 3 is hanging and being supported in the examination room. The X-ray tube 3 corresponds to the radiation source of the present invention and the FPD 4 corresponds to the detection means of the present invention.

Referring to FIG. 1, the X-ray tube control element 6 is installed in order to control the X-ray tube 3 with the predetermined tube electric current, the electric voltage and the pulse width. Such X-ray tube control element 6 according to the present invention plays functionally an important role. The inventor sets forth the detail thereof later. The X-ray tube control element 6 corresponds to the radiation source control means of the present invention.

An X-ray tube shifting mechanism 7a shifts the post 5 relative to the ceiling of the examination room. Such X-ray tube shifting mechanism 7a can shift the post 5 along the body axis of the subject M and also shift the post 5 along the side of the body of the subject M. The X-ray tube 3 hanging from and supported by the post 5 shifts following the shifting of the post 5. Therefore, the X-ray tube 3 is enabled to shift relative to the subject M on the table 2 by the X-ray tube shifting mechanism 7a. An X-ray tube shifting control element 8a is equipped to control the X-ray tube shifting mechanism 7a. According to the aspect of the Embodiment 1, it is given that the X-ray tube shifting mechanism 7a shifts only relative to the body axis of the subject M. The X-ray tube shifting mechanism 7a corresponds to the shifting means of the present invention. The X-ray tube shifting mechanism 7a acceleration shifts the suspended X-ray tube and transfers the X-ray tube to the constant-speed-shifting when the directive of imaging start is input to the operation panel 26.

The FPD shifting mechanism 7b shifts the FPD 4 underside of the table 2 relative to the table 2. Such X-ray FPD shifting mechanism 7b can shift the FPD 4 along the body axis of the subject M. Therefore, the FPD 4 is enabled to shift relative to the subject M on the table 2 by the FPD shifting mechanism 7b. The FPD shifting control element 8b is equipped to control the FPD shifting mechanism 7b. The FPD shifting mechanism 7b corresponds to the shifting means of the present invention. The FPD shifting mechanism 7b first acceleration-shifts the suspended FPD 4 and then transfers the FPD 4 to the constant-speed-shifting when the directive of imaging start is input to the operation panel 26.

The X-ray shifting mechanism 7a and the FPD shifting mechanism 7b shifts the X-ray tube and the FPD 4 in synchronization with each other relative to the subject M. Such X-ray tube shifting mechanism 7a and the FPD shifting mechanism 7b shifts the X-ray tube 3 in the straight, line along the straight-line trajectory (longitudinal direction of the table 2) parallel to the body axis direction A of the subject M in accordance with control by the X-ray tube shifting control element Ba and the FPD shifting control element 8b. The shift directions of the X-ray tube 3 and the FPD 4 coincide with the longitudinal direction of the table 2. The shifting directions of the X-ray tube 3 and the FPD 4 in synchronization with each other brought in reality by the X-ray tube shifting mechanism 7a and the FPD shifting mechanism 7b are opposite direction to each other. Accordingly, when the X-ray tube 3 shifts from the head of the subject M to the toe thereof the FPD 4 shifts from the toe of the subject M to the head thereof.

During the X-ray tube 3 and the FPD 4 are shifting in synchronization with each other, the cone-shaped X-ray beam irradiated from the X-ray tube 3 is always irradiated toward the target region of the subject M. Specifically, the irradiation angle of the X-ray beam can be changed e.g., from the initial angle −20° till the final angle 20° by changing angle of the X-ray tube 3. Specifically, the apparatus according to the present invention is structured as the X-ray beam irradiated from the X-ray tube 3 is always received onto the entire surface of the detection surface of the FPD 4 by tilting the X-ray tube 3. Such change of X-ray irradiation angle can be conducted by the X-ray tube inclination mechanism 9. The X-ray tube inclination control element 10 is installed so as to control the X-ray tube inclination mechanism 9.

Referring to FIG. 1, the X-ray tube 3 and the FPD 4 shift from the initial position illustrated as a solid line to the position illustrated as a dashed-line via the position illustrated as a broken line facing each other when the X-ray imaging apparatus according to the present invention generates a tomographic image. At this time, the X-ray tube 3 while shifting in synchronization with the FPD 4 irradiates pulsed X-ray beam 74 times, Such X-ray beams generate 74 X-ray images P1, P2, ..., P74. An image generation element 11 performs such image generation.

The image generation element 11 acquires the detection signal, of the X-ray output from the FPD 4 every irradiation of the X-ray and generates 74 X-ray images P1, P2, ..., P74. The generated images are sent out to the tomographic image generation element 12. The image generation element 11 corresponds to the image generation means of the present invention and the tomographic image generation element 12 corresponds to the tomographic image generation means of the present invention.

The tomographic image generation element 12 generates a tomographic image D obtained when the subject M is sliced at a sliced section by superimposing the series of X-ray images P1, P2, ..., P74 which are continuously imaged while the X-ray tube 3 and the FPD 4 are shifting in the opposite direction to each other, to each other based on the add and shift method.

<Principal of Add and Shift Method>

Figure 2:
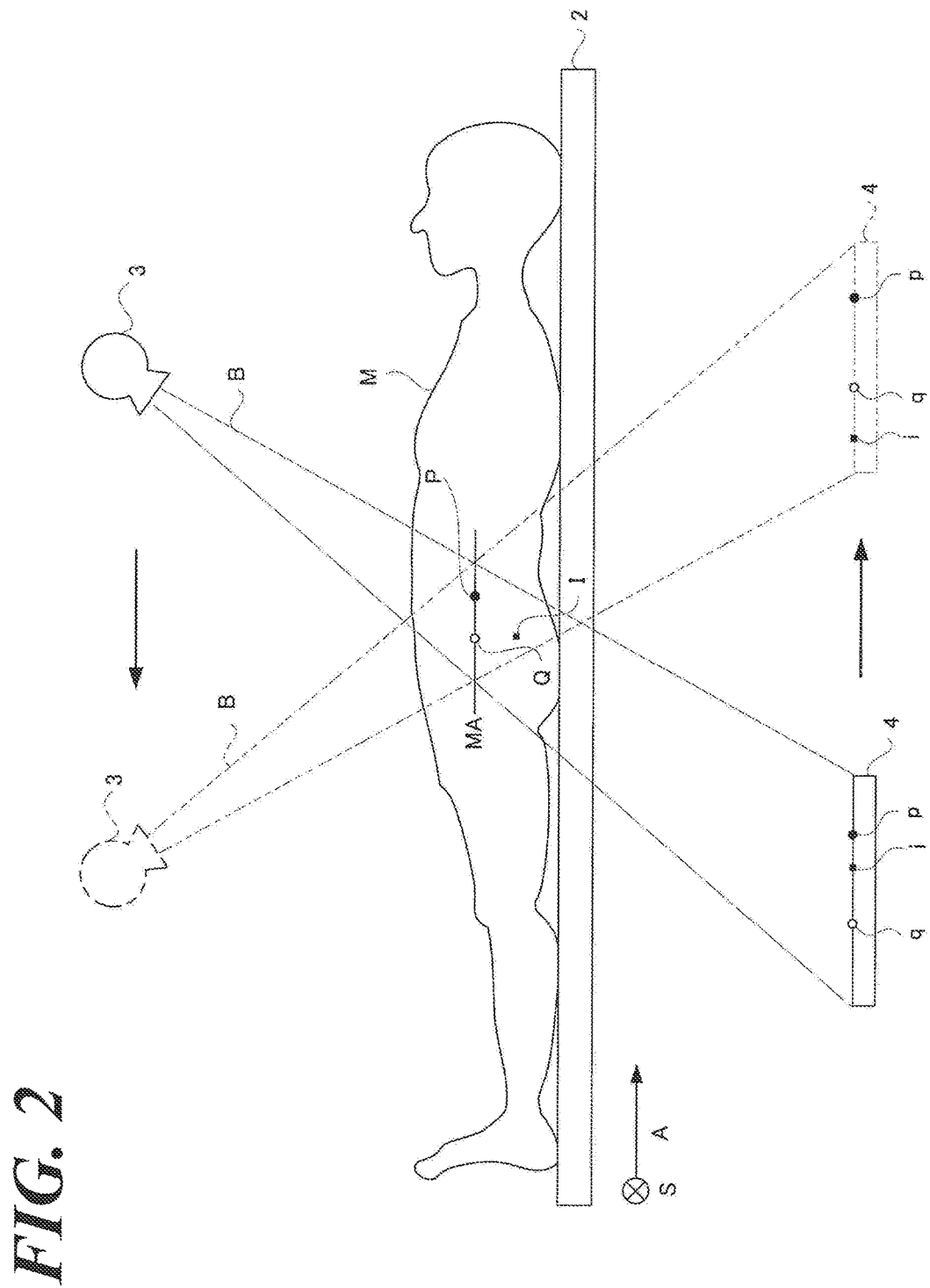
FIG. 2 is a schematic diagram illustrating a generation principle of the tomographic image of Embodiment 1.

FIG. 2 is illustrating the principal of add and shift method which the tomographic image generation element 12 applies. For example, referring to FIG. 2, as the virtual plan (the base slice section MA) parallel to the table 2 (horizontal relative to the perpendicular) is set forth, a series of the X-ray images P is generated by the image generation element 11 while the FPD 4 moves in synchronization in the opposite direction with the X-ray tube 3 according to the radiation direction of the cone shaped X-ray beam from the X-ray tube 3 so that the points p, q in-place on the base slice section can be always projected to the fixed-points p, q on the X-ray detection surface of the FPD 4.

The projection images of the subject M are incorporated into the series of the X-ray images P while changing the position thereof. Then, providing the series of X-ray images P is reconstructed by the tomographic image generation element 12, the images (e.g., fixed point p, q) in-place on the base slice section MA are cumulated and the X-ray tomographic image can be taken.

On the other hand, the point I in-place out of the base slice section MA is incorporated into the series of images of the subject as a point i while changing the projection position on the FPD 4. Such point i, differently from the fixed points p, q, is out of focus at the step of superimposing the X-ray projection images by the tomographic image generation element 12 without forming an image. Accordingly, the series of projection images are superimposed, so that the X-ray tomographic image incorporating only the image in-place on the base slice section MA of the subject M can be obtained. Accordingly, the projection images are simply superimposed, so that the tomographic image on the base slice section MA can be obtained.

Further, the tomographic image generation element 12 is able to obtain the same tomographic image at any slice section horizontal to the base slice section MA. During imaging, the projection position of the point i relative to the FPD 4 shifts but the shifting rate increases according to increasing distance between the point I before projection and the base slice surface MA. Utilizing such fact, providing the obtained series of images of the subject should be reconstructed while shifting to the body axis direction A at the predetermined pitch, the tomographic image at the slice section parallel to the base slice section MA can be obtained.

[Other Structures of the X-Ray Imaging Apparatus 1]

The main control element 25 comprises a CPU and brings each element 6, 8a, 8b, 10, 11, 12 into reality by executing a variety of programs. In addition, a separated individual control device can control each element to bring into reality. The memory element 23 stores all parameters needed to control the operation of the X-ray imaging apparatus 1 according to the Embodiment 1. The operation panel 26 is used for the operator to input a variety of directives such as start of imaging. The display element 27 is installed to display a tomographic image D for diagnosis. The memory element 23 corresponds to the memory means of the present invention and the operation panel 26 corresponds to the input means of the present invention.

[The Most Characteristic Structure of the Present Invention]

Figure 3:
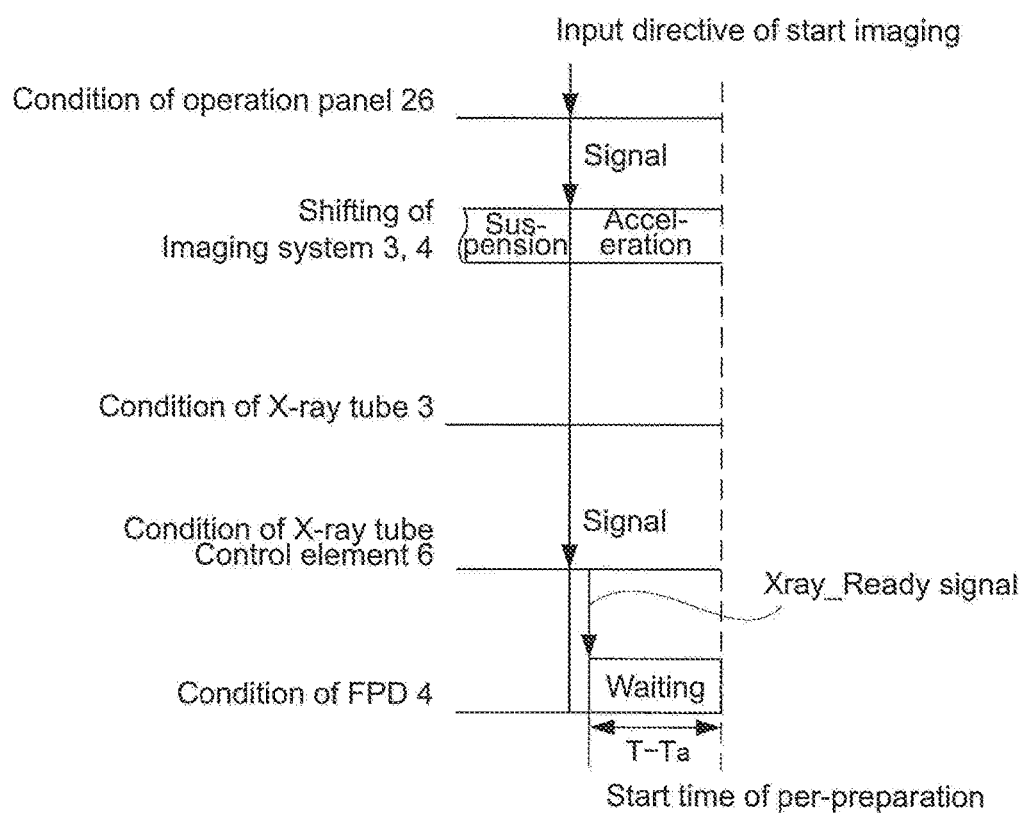
FIG. 3 is a timing chart illustrating an operation of the X-ray imaging apparatus according to the aspect of the Embodiment 1.

The inventor sets forth the most characteristic structure of the present invention. In brief, the feature of the present invention is that the FOD 4 and the X-ray tube control element 6 work in concert each other to start imaging a series of X-ray images P1, P2, . . . , P74 at an adequate timing. FIG. 3 is the timing chart illustrating varying condition of each element in chronological order when the operator inputs the directive through the operation panel 26 to start imaging a tomographic image D. Referring to FIG. 3, the X-ray tube 3 and the FPD 4 are suspending until the operator operates the operation panel 26. Here, the X-ray tube 3 and the FPD 4 are collectively called an imaging system 3, 4.

When the operator inputs the directive to start imaging through the operation panel 26, the signal indicating such directive is sent out from the operation panel 26 to the X-ray tube shifting control element 8a and the FPD shifting control element 8b which shift the imaging system 3, 4 the X-ray tube shifting control element 8a and the FPD shifting control element 8b starts shifting the imaging system 3, 4 in accordance with such signal. A preferable shifting mode of the imaging system 3, 4 to take continuously the X-ray images P1, P2, . . . , P74 is a constant-speed-shifting. The imaging system 3, 4, however, is suspending when the directive is given to start imaging. Therefore, the imaging system 3, 4 must be accelerated once prior to the constant-speed-shifting. Specifically, such shifting start of the imaging system 3, 4 is the same as an acceleration start of the imaging system 3, 4.

When the operator inputs the directive to start imaging through the operation panel 26, the signal indicating such directive is also sent out from the operation panel 26 to the X-ray tube control element 6. The X-ray tube control element 6, when receives the signal, requests the X-ray tube 3 for the data indicating the condition of the X-ray tube 3, and then when confirms that the condition of the X-ray tube 3 is normal for irradiation of X-ray, the X-ray tube control element 6 sends out the Xray_Ready signal, indicating that X-ray irradiation is available, to the FPD 4. Such Xray_Ready signal is the signal to notify the completion of preparation for X-ray irradiation and sent out continuously to the FPD 4 until the imaging of the series of the X-ray images P1, P2, . . . , P74 is completed. Nevertheless, referring to FIG. 3, the Xray_Ready signal is illustrated as a trigger signal output from the X-ray tube control element 6 to the FPD 4. In such way, the X-ray tube control element 6 sends out the signal indicating that the X-ray tube is able to irradiate an X-ray to the FPD 4 when the directive to start imaging is input to the operation panel 26.

When receives the Xray_Ready signal from the X-ray tube control element 6, the FOD 4 realizes that the X-ray irradiation is being carried out in the future and executes the pre-preparation needed to detect the X-ray. Such pre-preparation requires, e.g., relatively long time more or less 100 msec. Such time is extremely long compared to the time which the X-ray tube control element 6 that receives the signal from the operation panel 26 needs to output the Xray_Ready signal.

On the other hand, the FPD 4 is not designed so as to start the pre preparation momentarily right after receiving the Xray_Ready signal. The FPD 4 starts the pre-preparation as the time when the pre-preparation is completed coincides with the time when the acceleration of the imaging system 3, 4 is over. The time from when the Xray_Ready signal is output to when the acceleration of the imaging system 3, 4 is over is e.g., approximately 500 msec and the pre-preparation needs e.g., 100 msec, so that the FPD 4 can start the pre-preparation at the time when e.g., 400 msec passes after the Xray_Ready signal is received. The FPD 4 sustains the waiting condition until the pre-preparation starts.

FIG. 3 is indicating the time when the FPD 4 starts the pre-preparation. The inventor sets forth how the FPD 4 can confirm the time when the pre-preparation starts. The memory element 23 stores the shifting waiting time T indicating the time from when the FPD 4 receives the Xray_Ready signal from the X-ray tube control element 6 until when the X-ray tube 3 and the FPD 4 transfer to the constant-speed-shifting. Such shifting waiting time T can be obtained by measuring approximately how long the suspended imaging system 3, 4 takes to transfer to the constant-speed-shifting. Such time is the time needed for the suspended imaging system 3, 4 to reach the constant-shifting speed while increasing speed. i.e. the time while the imaging system 3, 4 is acceleration-shifting. The actual shifting waiting time T is e.g., 500 msec, but such time can be arbitrarily changed depending on the shifting mode of the imaging system 3, 4. In addition, the memory element 23 stores also the pre-preparation time Ta which the FPD 4 needs to detect an X-ray. Such pre-preparation time Ta is the time which is set up as the operation of the FPD 4. The FPD 4 reads out the shifting waiting time T and the pre-preparation time Ta from the memory element 23 prior to staring imaging. The pre-preparation time Ta of the FPD 4 is e.g., 100 msec. The FPD 4 starts the pre-preparation, which takes 100 msec for the pre-preparation time, after the T-Ta=400 msec (waiting time for execution of pre-preparation) passes from the time when the Xray_Ready signal is output from the X-ray tube control element 6.

The pre-preparation carried out by the FPD 4 is mainly an operation in which the charge carriers cumulated in the respective detection elements forming the FPD 4 are released. The FPD 4 has a property in which the charge carrier is gradually cumulated in the detection element without irradiating the X-ray due to an electric current leak in the conversion layer. Accordingly, the charge carriers cumulated in the respective detection elements must be released just before the X-ray is irradiated. Such operation is called a reset operation. The only just once reset operation is not enough prior to X-ray irradiation and must be performed right before the X-ray irradiation. For example, when the X-ray irradiation is not executed within 50 msec after the reset operation is implemented, no clear images P1, P2, . . . , P74 are obtained. According to the apparatus of the present invention, the X-ray detection starts right after the pre-preparation is completed, so that such above problem does not take place.

The operations of the FPD 4 are summarized as below. Specifically, the FPD 4 according to the present invention not only starts the pre-preparation upon X-ray detection while the X-ray tube 3 and the FPD 4 are acceleration-shifting, but also completes the pre-preparation of the FPD 4 in according with a while in which the X-ray tube shifting mechanism 7a and the FPD shifting mechanism 7b acceleration-shift the X-ray tube 3 and the FPD 4 and transfers to the condition in which the X-ray becomes detectable. Given the time when the X-ray tube shifting mechanism 7a and the FPD shifting mechanism 7b complete acceleration-shifting of the X-ray tube 3 and the FPD 4 and the time when the pre-preparation of the FPD 4 is completed are different each other, a while of unwanted X-ray detection period occurs or a while to detect X-ray cannot be ensured, so that the image quality of X-ray images P1, P2, . . . , P74 can be influenced. Relative to the apparatus according to the present invention, the two timings are coincidental, so that no such problem takes place.

Figure 4:
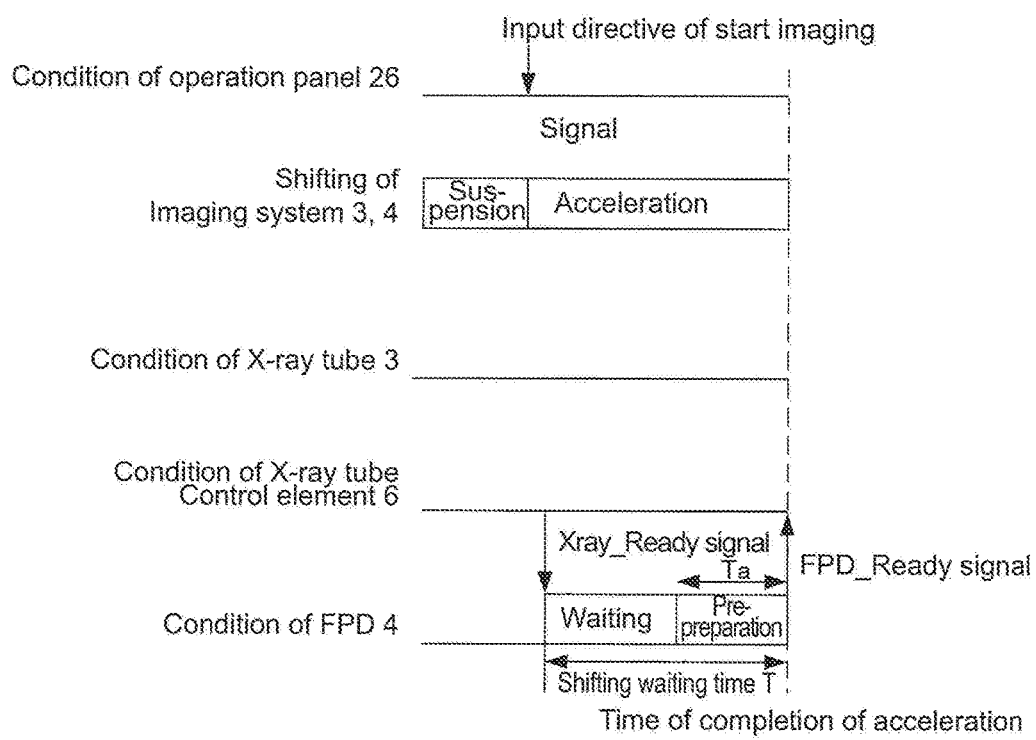
FIG. 4 is a timing chart illustrating an operation of the X-ray imaging apparatus according to the aspect of the Embodiment 1.

FIG. 4 is illustrating the time when acceleration of the imaging system 3, 4 is over. Acceleration-shifting of the imaging system 3, 4 according to the present invention is over at the same time and the imaging system 3, 4 transfers to the constant-speed-shifting from the time when the acceleration-shifting is over. The X-ray tube shifting control element 8a and the FPD shifting control element 8b bring the control of shifting speed into the reality. On the other hand, when completes the pre-preparation, the FPD 4 sends back the FPD_Ready signal, indicating that the X-ray is detectable, to the X-ray tube control element 6 when the FPD 4 is confirmed normal. Such FPD_Ready signal is the signal to permit X-ray irradiation and sent out continuously to the X-ray tube control element 6 until imaging the series of the X-ray images P1, P2, . . . , P74 is completed. Nevertheless, referring to FIG. 4, the FPD_Ready signal is illustrated as a trigger signal output from the FPD 4 to the X-ray tube control element 6. In addition, at this time, the pre-preparation of the FPD 4 is completed and transfers to the mode in which an X-ray is detected.

Figure 5:
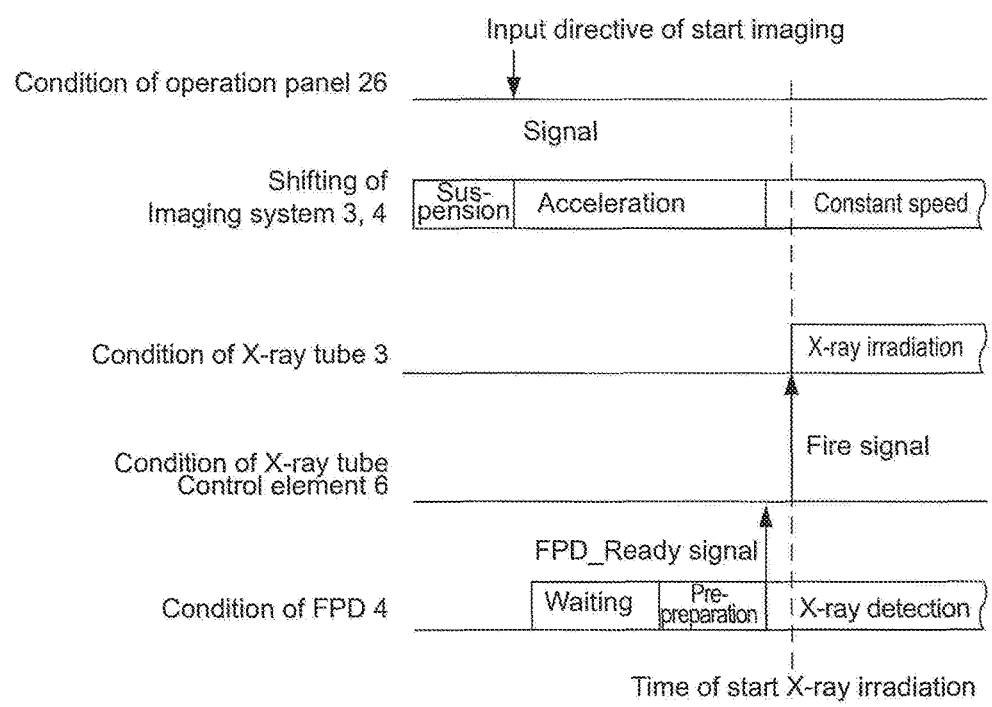
FIG. 5 is a timing chart illustrating an operation of the X-ray imaging apparatus according to the aspect of the Embodiment 1.

FIG. 5 is illustrating the time when the X-ray is irradiated when further the time is passed after the condition illustrated in FIG. 4. The X-ray tube control element 6 receiving the FPD_Ready signal from the FPD 4 sends out the Fire signal, indicating the directive to start the irradiation, to the X-ray tube 3. The X-ray tube 3 starts to irradiate an X-ray based on such Fire signal. The irradiated X-ray is incident into the FPD 4 which already has transferred to the X-ray detection mode. The time when the X-ray is irradiated is already the time after the imaging system 3, 4 are transferred to the constant-speed-shifting. A while needed from receiving the FPD_Ready signal to sending the Fire signal is extremely short compared to a while needed for pre-preparation of the FPD 4. Accordingly, imaging of a series of X-ray images P1, P2, . . . , P74 starts.

Figure 6:
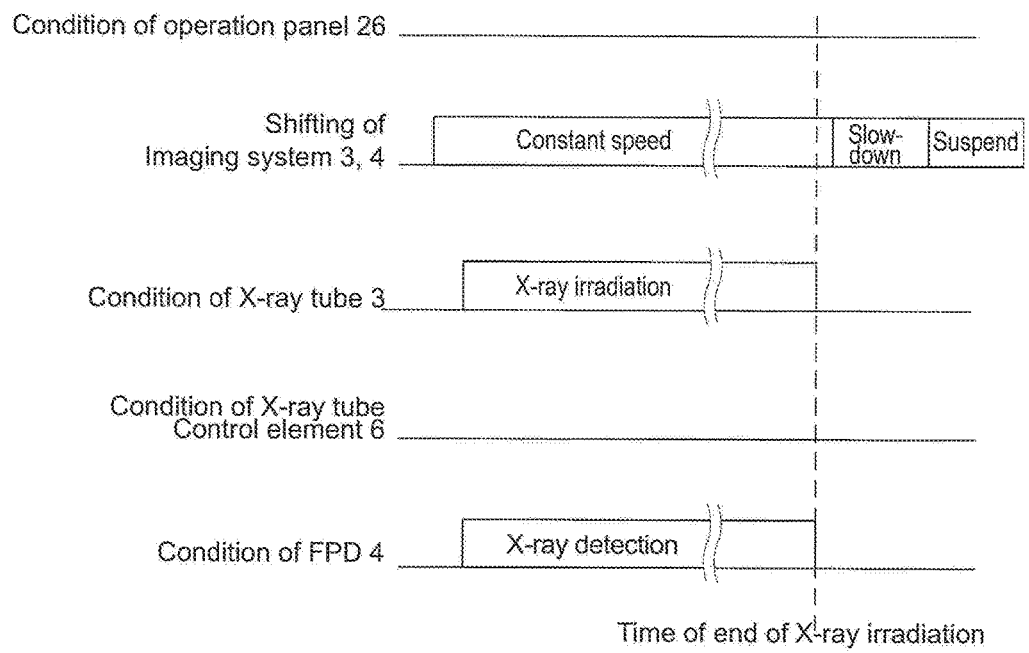
FIG. 6 is a timing chart illustrating an operation of the X-ray imaging apparatus according to the aspect of the Embodiment 1.
Figure 7:
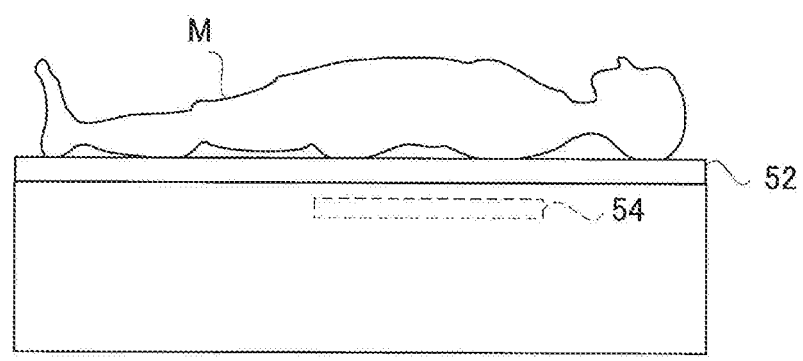
FIG. 7 is a schematic diagram illustrating a conventional radiography apparatus.
Figure 8:
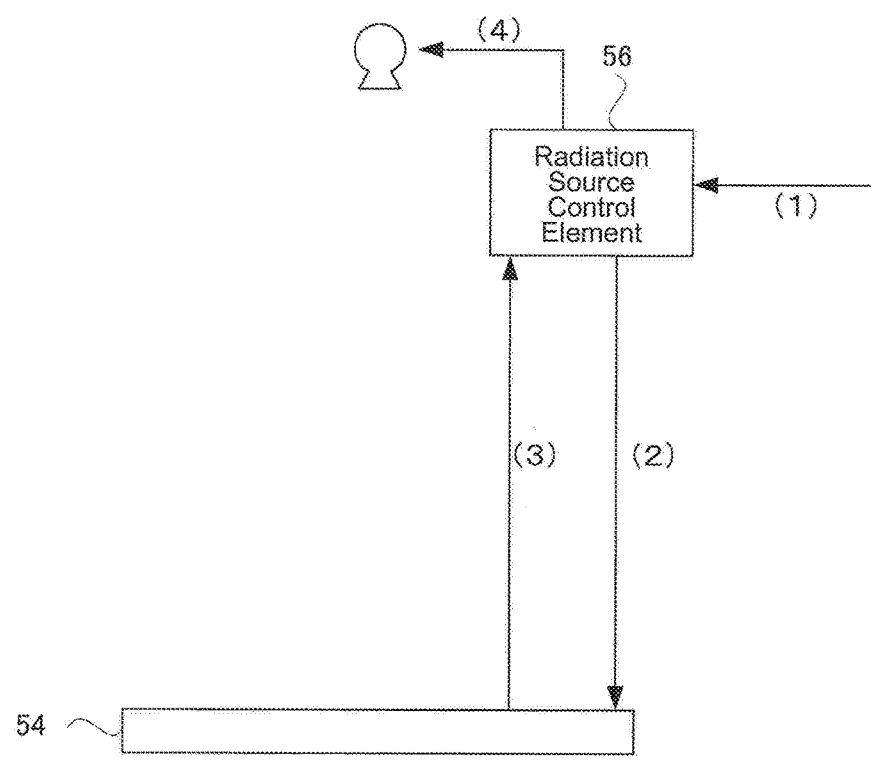
FIG. 8 is a schematic diagram illustrating an operation of a conventional radiography apparatus.
Figure 9:
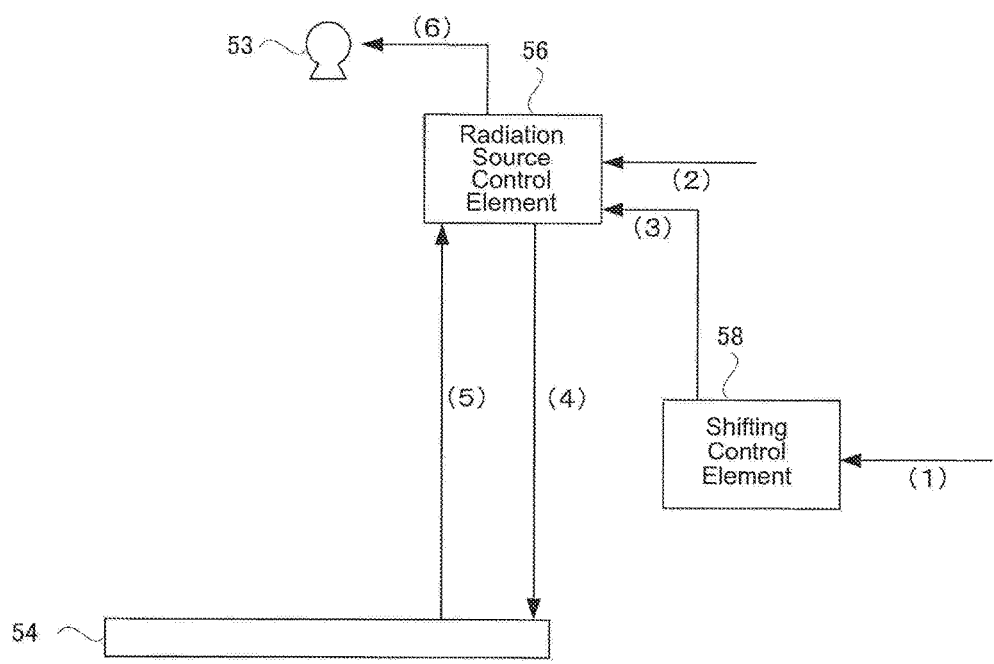
FIG. 9 is a schematic diagram illustrating a problem of a conventional radiography apparatus.
Figure 10:
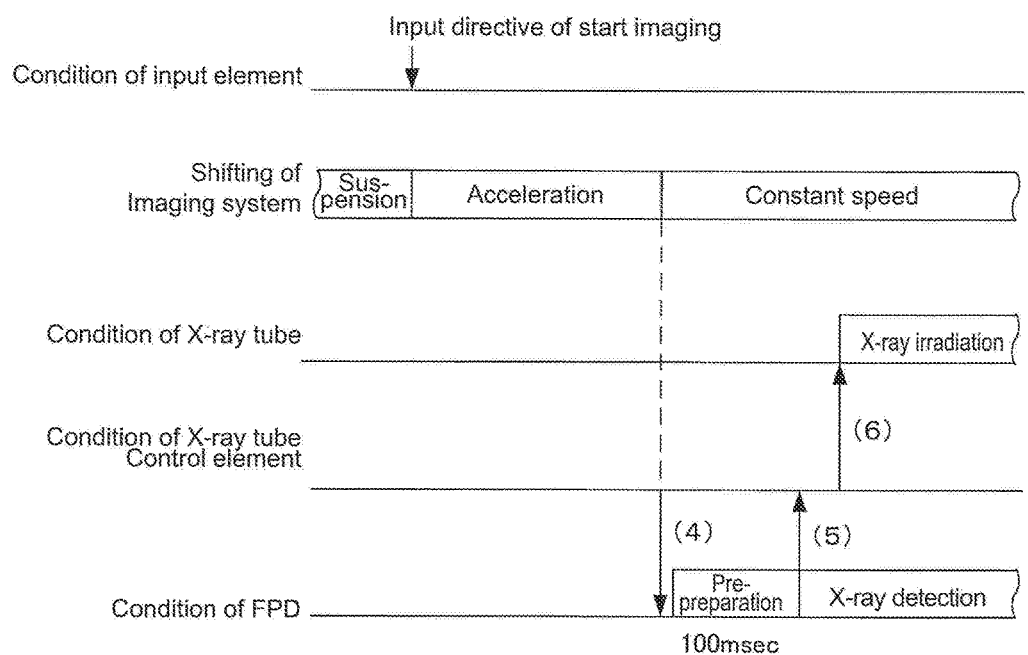
FIG. 10 is a schematic diagram illustrating a problem of a conventional radiography apparatus.

FIG. 6 is illustrating the time when imaging operation relative to the series of X-ray images P1, P2, . . . , P74 is completed. The imaging system 3, 4 shifting at the constant speed slows down after a while and suspends. The series of X-ray images P1, P2, . . . , P74 are all taken while the imaging system 3, 4 is shifting in the constant speed. In addition, relative to the illustration of FIG. 6, the X-ray irradiation is illustrated as if continuous with the constant intensity, but the actual X-ray irradiation is pulsed corresponding to the imaging of the series of X-ray images P1, P2, . . . , P74. In addition, relative to the illustration of FIG. 6, the X-ray detection is illustrated as if taking place just once in the continuous imaging of the series of X-ray images P1, P2, . . . , P74, but the actual X-ray detection is repeatedly implemented corresponding to the imaging of the series of X-ray images P1, P2, . . . , P74. The FPD 4 sends out the detection data relative to the X-ray images P1, P2, . . . , P74 by repeating X-ray detection and read-out of the detection data to the image generation element 11.

Figure 11A:
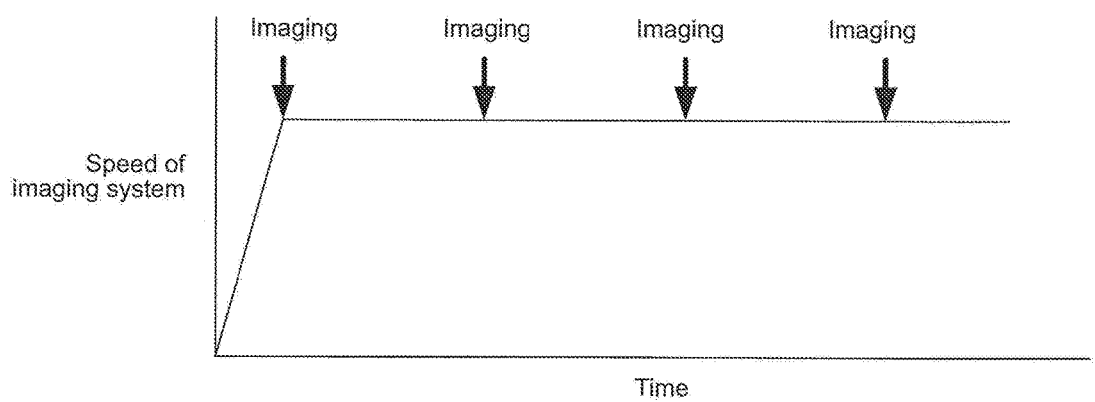
FIG. 11A, 11B are schematic diagrams illustrating a problem of a conventional radiography apparatus.
Figure 11B:
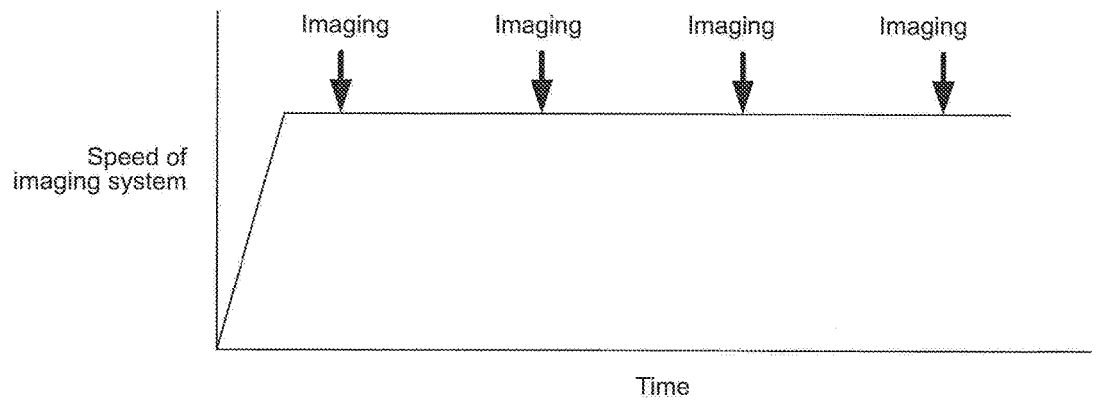

According to the present invention, when imaging of X-ray images P1, P2, . . . , P74 is implemented, the imaging of the series of X-ray images P1, P2, . . . , P74 can be completed as illustrated in FIG. 11A at the ideal timing.

According to the present invention, the radiation imaging apparatus not subject to a delayed imaging due to the effect of the pre-preparation of the FPD 4 can be provided. According to the present invention, the FPD 4 starts the pre-preparation for the radiation detection while the X-ray tube 3 or the FPD 4 are acceleration-shifting following receiving the signal from the FPD 4. Specifically, according to the present invention, acceleration-shifting of the X-ray tube 3 or the FPD 4 and the pre-preparation on the X-ray detection are implemented simultaneously. Therefore, differently from the conventional device, the imaging is available right after start of constant-speed-shifting without start of the pre-preparation of the FPD 4 following start of constant-speed-shifting of the X-ray tube 3 or the FPD 4. Consequently, no effect due to the delayed imaging appears in the X-ray images P1, P2, . . . , P74.

The present invention is not limited to the above structure and farther following alternative Embodiment can be implemented.

(1) According to the above structure, the X-ray tube 3 shifts in synchronization with the FPD 4, but the structure of the present invention is not limited thereto. Instead of the above structure, the aspect of the present invention can be applied to the structure in which only the X-tube 3 shifts or in which only the FPD 4 shifts.

(2) According to the above structure, the X-ray tube 3 and the FPD 4 shift in the opposite direction to each other, but the structure of the present invention is not limited thereto. The aspect of the present invention can be also applied to an imaging method in which a series of X-ray images is taken while the X-ray tube 3 and the FPD 4 are shifting in the same direction keeping the locational relationship in-between. Such imaging method is applied to implement long-length imaging in some case.

(3) According to the above structure, the FPD 4 sends back the FPD_Ready signal at the time when the pre-preparation for X-ray detection is completed, but the present invention is not limited thereto. The FPD 4 can send back the FPD_Ready signal as a trigger in which the FPD 4 receives the signal indicating the start time of constant-speed-shifting from the X-ray tube shifting control element 8a and the FPD shifting control element 8b following the completion of the pre-preparation. Also, the FPD 4 according to the above structure implements the pre-preparation of the FPD 4 at the time when the pre-preparation waiting time T-Ta passes from the time when receiving the Xray_Ready signal from the X-ray tube control element 6, but the present invention is not limited thereto. The pre-preparation of the FPD 4 starts as a trigger in which the FPD 4 receives the Xray_Ready signal at the time when the pre-preparation waiting time T-Ta passes from the start time of the constant-speed-shifting from the X-ray tube shifting control element 8a and the FPD shifting control element 8b and then the FPD_Ready signal can be sent to the X-ray tube control element 6.

(4) According to the above structure, the time when the X-ray tube 3 or the FPD 4 complete the acceleration-shifting coincides with the time when the pre-preparation of the FPD 4 is completed, but both times are not mandatory to be the same. Given the difference between the time when the X-ray tube 3 or the FPD 4 complete the acceleration-shifting and the time when the pre-preparation of the FPD 4 is completed is small enough, the effect due to the incident in which the while of unwanted X-ray detection period occurs or the while to detect X-ray cannot be ensured is small enough, so that the effect on the image quality of X-ray images P1, P2, . . . , P74 can be ignored.

INDUSTRIAL APPLICABILITY

As set forth above, the above invention is suitable for medicinal field,

REFERENCE OF SIGNS

3 X-ray tube (Radiation source)
4 FPD (Detection means)
6 X-ray tube control element (Radiation source control means)
7a X-ray shifting mechanism (Shifting means)
7b FPD shifting mechanism (Shifting means)
11 Image generation element (Image generation means)
12 Tomographic image generation element (Tomographic image generation means)
23 Memory element (Memory storage means)
26 Operation panel It will be further understood by those of skill in the art that the apparatus and devices and the elements herein, including any radiography apparatus, without limitation, and including the sub components such as operational structures, circuits, communication pathways, and related elements, control elements of all kinds, display circuits and display systems and elements, any necessary driving, elements, inputs, sensors, detectors, memory elements, processors and any combinations of these structures etc. as will be understood by those of skill in the art as also being identified as or capable of operating the systems and devices and subcomponents noted herein and structures that accomplish the functions without restrictive language or label requirements since those of skill in the art are well versed in related X-Ray diagnostic devices, computer and operational controls and technologies of radiographic devices and all their sub components, including various circuits and combinations of circuits without departing from the scope and spirit of the present invention.

Although only a few embodiments have been disclosed in detail above, other embodiments are possible and the inventors intend these to be encompassed within this specification. The specification describes certain technological solutions to solve the technical problems that are described expressly and inherently in this application. This disclosure describes embodiments, and the claims are intended to cover any modification or alternative or generalization of these embodiments which might be predictable to a person having ordinary skill in the art.

Those of skill would further appreciate that the various illustrative logical blocks, modules, circuits, and algorithm steps described in connection with the embodiments disclosed herein may be implemented as electronic hardware, computer software running on a specific purpose machine that is programmed to carry out the operations described in this application, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each, particular application, but such implementation decisions should not be interpreted as causing a departure from the scope of the exemplary embodiments.

In one or more exemplary embodiments, the functions described may be implemented in hardware, software, firmware, or any combination thereof if implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer.

The memory storage can also be rotating magnetic hard disk drives, optical disk drives, or flash memory based storage drives or other such solid state, magnetic, or optical storage devices, or in any other suitable medium for memory storage. The computer readable media can be an article comprising a machine-readable non-transitory tangible medium embodying information indicative of instructions that when performed by one or more machines result in computer implemented operations comprising the actions described throughout this specification.

Operations as described herein can be carried out on or over a web site or wireless network of any kind. The website can be operated on a server computer, or operated locally, e.g., by being downloaded to the client computer, or operated via a server farm. The website can be accessed over a mobile phone or a PDA, or on any other client. The website can use HTML code in any form, e.g., MHTML, or XML, and via any form such as cascading style sheets ("CSS") or other.

The computers or processors described herein may be any kind of computer or processor, either general purpose, or some specific purpose computer such as a workstation. The programs may be written in C, or Java, Brew or any other programming language. The programs may be resident on a storage medium, e.g., magnetic or optical, e.g. the computer hard drive, a removable disk or media such as a memory stick or SD media, or other removable medium. The programs may also be run over a network, for example, with a server or other machine sending signals to the local machine, which allows the local machine to carry out the operations described herein.

Also, the inventors intend that only those claims which use the words "means for" are intended to be interpreted under 35 USC 112, sixth paragraph. Moreover, no limitations from the specification are intended to be read into any claims, unless those limitations are expressly included in the claims.

Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

What is claimed is:

1. A radiography apparatus, comprising:
a radiation source that irradiates a radiation to a subject;
a detection unit that detects said radiation transmitted through said subject;
an input unit that allows an operator to input a directive to said radiographic apparatus to start imaging;
a shifting unit that first acceleration-shifts said radiation source under suspension or said detection unit under suspension and then transfers into a constant-speed-shifting when a directive of a start imaging start is input to said input unit; and
a radiation source control unit that sends out a signal, which indicates that said radiation source is ready, to irradiate said radiation, to said detection unit when said directive of start imaging is input to said input unit;
wherein said detection unit transfers into the radiation detectable state promptly after said radiation source or said detection unit transfers into constant-speed-shifting by starting a pre-preparation for radiation detection while said radiation source or said detection unit is acceleration-shifting.

2. A radiography apparatus, comprising:
the radiography apparatus according to claim 1, wherein:
said detection unit sends back a signal, which indicates that a radiation detection is available, to said radiation source control unit.

3. The radiography apparatus, according to claim 2, wherein:
said detection unit further comprising:
a memory unit that stores a shifting waiting time between a time when a signal is received from said radiation source control unit and a time when said radiation source or said detection unit transfers to a constant-speed-shifting and a pre-preparation time for said pre-preparation for said detection means to detect said radiation; and
wherein said detection unit starts said pre-preparation at g time after a time obtained by subtracting said pre-preparation time from said shifting waiting time is passed from a time when receiving a signal from said radiation source control unit and implementing a send-back operation is when said pre-preparation is completed.

4. The radiography apparatus, according to claim 1, wherein:
a first time period in which said shifting unit is acceleration-shifting said radiation source or said detection unit is longer than a second time period in which said detection unit needs for said pre-preparation for radiation detection.

5. The radiography apparatus, according to claim 1 further comprising:
an image generation unit that generates a radiation image based on an output from said radiation detection unit; and
a tomographic image generation unit that generates a tomographic image by superimposing a series of radiographs to each other; and
wherein said series of radiographs are continuously imaged while said radiation source and said detection unit are shifting in a opposite direction from each other.

* * * * *